United States Patent
Krause et al.

(10) Patent No.: US 9,943,442 B2
(45) Date of Patent: Apr. 17, 2018

(54) APPARATUS AND METHOD FOR CREATING INCISIONS IN A HUMAN CORNEA

(71) Applicant: Wavelight Gmbh, Erlangen (DE)

(72) Inventors: Johannes Krause, Nuremberg (DE); Christof Donitzky, Eckental (DE)

(73) Assignee: Wavelight GmbH (DE)

( * ) Notice: Subject to any disclaimer, the term of this patent is extended or adjusted under 35 U.S.C. 154(b) by 0 days.

(21) Appl. No.: 14/772,116

(22) PCT Filed: Mar. 8, 2013

(86) PCT No.: PCT/EP2013/054744
§ 371 (c)(1),
(2) Date: Sep. 2, 2015

(87) PCT Pub. No.: WO2014/135218
PCT Pub. Date: Sep. 12, 2014

(65) Prior Publication Data
US 2016/0008173 A1     Jan. 14, 2016

(51) Int. Cl.
*A61F 9/008* (2006.01)

(52) U.S. Cl.
CPC .......... *A61F 9/00836* (2013.01); *A61F 2009/00855* (2013.01); *A61F 2009/00872* (2013.01); *A61F 2009/00897* (2013.01)

(58) Field of Classification Search
CPC .. A61F 2009/00872; A61F 2009/00897; A61F 9/00836
USPC ............................................. 600/2, 4–5, 10
See application file for complete search history.

(56) References Cited

U.S. PATENT DOCUMENTS

| | | |
|---|---|---|
| 6,902,561 B2 | 6/2005 | Kurtz et al. |
| 7,189,224 B2 | 3/2007 | Kurtz et al. |
| 2003/0212387 A1* | 11/2003 | Kurtz ............... A61F 9/008 606/4 |

(Continued)

FOREIGN PATENT DOCUMENTS

| | | |
|---|---|---|
| WO | 03/082146 A2 | 10/2003 |
| WO | 2011/088848 A1 | 7/2011 |

OTHER PUBLICATIONS

Ella Faktorovich MD; "Lasik With AMO Femtosecond Lasers: Laser Settings" Chapter 4; Femtodynamics: A guide to Laser Settings and Procedure Techniques to Optimize Outcomes with Femtosecond Lasers; Published 2009; pp. 29-58.

*Primary Examiner* — Lynsey Eiseman
*Assistant Examiner* — Jonathan Kuo
(74) *Attorney, Agent, or Firm* — Keiko Ichiye

(57) ABSTRACT

An apparatus for creating incisions in a human cornea comprises: a source of pulsed laser radiation; a scanner device for scanning the laser radiation; and a control computer for controlling the scanner device based on a control program, the control program containing instructions that, when executed by the computer, bring about the creation in the cornea of: a flap cut defining a corneal flap that is connected to surrounding corneal tissue through a hinge; and one or more auxiliary cuts in connection with the flap cut for removing gas generated during creation of the flap cut, the one or more auxiliary cuts defining a first channel extending from the flap cut to an anterior surface of the cornea and a reservoir located at least partially deeper within the cornea than the flap cut.

30 Claims, 3 Drawing Sheets

(56) References Cited

U.S. PATENT DOCUMENTS

2011/0184394 A1\* 7/2011 Donitzky ............... A61F 9/008
  606/5
2016/0213517 A1\* 7/2016 Martin ............... A61F 9/00836

\* cited by examiner

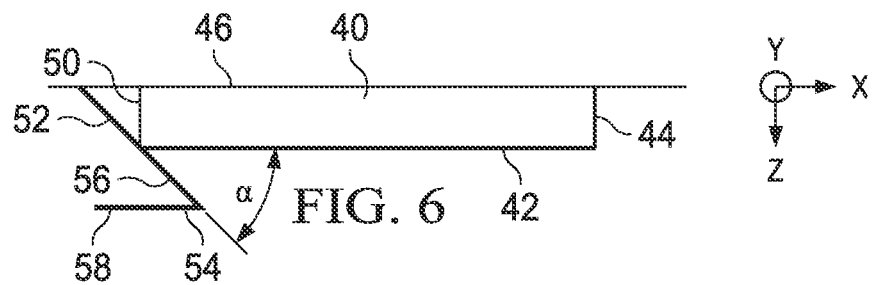
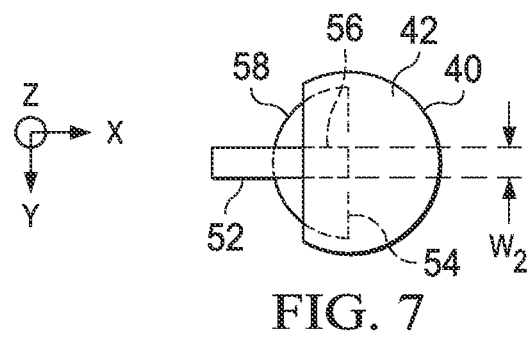
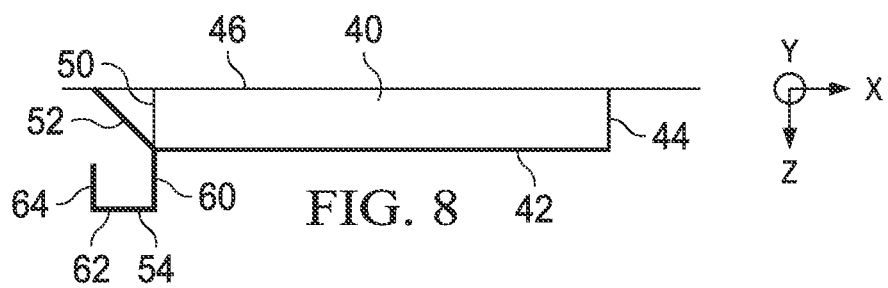
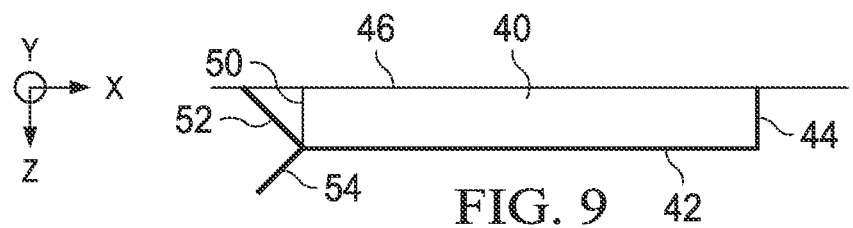

APPARATUS AND METHOD FOR CREATING INCISIONS IN A HUMAN CORNEA

CROSS REFERENCE TO RELATED APPLICATIONS

This application is a section 371 national stage phase of International Application No. PCT/EP2013/054744, filed 8 Mar. 2013, titled "APPARATUS AND METHOD FOR CREATING INCISIONS IN A HUMAN CORNEA," which is hereby incorporated by reference in its entirety.

The present disclosure is concerned with the creation of incisions in a human cornea using pulsed, focused laser radiation. More specifically, the present disclosure relates to the preparation of a LASIK flap in a human cornea whilst avoiding the generation of an opaque bubble layer (OBL).

A frequently employed technique for eliminating visual defects of the human eye (e.g., myopia or hyperopia or astigmatism) is referred to as LASIK (Laser in-situ Keratomileusis). LASIK is a technique in which a small cover disc in the cornea is cut free, which cover disc remains connected to surrounding corneal tissue through a hinge, so that the cover disc can be folded aside to expose the underlying tissue regions of the cornea and can be folded back following an ablation process performed on the exposed tissue regions using UV laser radiation. The cover disc is conventionally referred to as a flap in the related art. On account of the removal of stromal material by the ablation process, a changed shape of the anterior surface of the cornea results after the flap has been folded back. The changed shape of the anterior corneal surface results in a different refractive behavior of the cornea and consequently of the overall imaging system of the eye. Suitable definition of the ablation profile ensures that the initial visual defect is at least distinctly attenuated and, at best, is almost completely eliminated.

For the generation of an incision using pulsed laser radiation in transparent or translucent material (i.e. transparent/translucent to the laser radiation), the so-called laser-induced optical breakdown (LIOB) is known as a physical effect. The breakdown ultimately results in a photodisruption of the irradiated tissue in the region of the focus of the laser radiation. The interaction of the radiation and the irradiated tissue causes a local vaporization of the tissue at the focal point. Gases may arise as a result, wherein the gases—to the extent that they are not conducted away to the outside—collect in internal cavities or are absorbed by the adjoining material. It has been found that in the course of LASIK treatments of the human eye, a residence in the cornea of the gases arising during the creation of the flap can lead to problems in the course of a subsequent laser ablation. More specifically, it has been found that the gases may lead to the generation of what is frequently referred to in the pertinent art as an opaque bubble layer (OBL). A problem that may be associated with the generation of an OBL is that precise tracking of the eye by means of an eye-tracker may be complicated or even rendered impossible by the presence of an OBL. In this regard, it is to be understood that laser systems employed for the ablation of corneal tissue (such as in a LASIK treatment) are conventionally equipped with an eye-tracker, in order to detect eye movements during the ablative laser treatment and to reposition the laser radiation correspondingly. An eye-tracker usually includes at least one camera and suitable image-processing software for processing the images recorded by the camera and detecting changes in the position of the eye. The image-processing software may evaluate one or more characteristic eye features including, but not limited to, characteristic points of the iris, a pupillary center, a corneal apex, the limbus, etc. It has been found that accumulations of gas remaining in the cornea, which have arisen in the course of preparation of the flap, can impede the acquisition of such characteristic eye features by an eye-tracker.

WO 2011/088848 A1 discloses a technique for reducing OBL generation during LASIK treatments by means of an auxiliary incision that forms a channel extending between a bed cut of a flap incision and the anterior surface of the eye. The channel allows gases generated during laser creation of the flap incision to be discharged outwardly, i.e. to the exterior of the eye.

Another solution to address the problem of a cloudy appearance of the cornea as a result of gas generation during the photodisruption process has been proposed in US 2003/0212387 A1. This document discloses the generation of a pocket within the stromal tissue of the cornea, which pocket serves as a reservoir for operation gases.

It is an object of the invention to provide an improved apparatus and method for the creation of a flap incision in a human cornea, which apparatus and method reduce the risk of OBL generation during laser creation of the flap.

The present invention provides an apparatus for creating incisions in a human cornea, the apparatus comprising: a source of pulsed laser radiation; a scanner device for scanning the laser radiation; a control computer for controlling the scanner device based on a control program, the control program containing instructions that, when executed by the computer, bring about the creation in the cornea of a flap cut defining a corneal flap that is connected to surrounding corneal tissue through a hinge, and one or more auxiliary cuts in connection with the flap cut for removing gas generated during creation of the flap cut, wherein the one or more auxiliary cuts define a first channel extending from the flap cut to an anterior surface of the cornea and a reservoir located at least partially deeper within the cornea than the flap cut.

In an embodiment, the reservoir is connected with the first channel.

In an embodiment, locations of connection of the reservoir and the first channel with the flap cut are at least partially overlapping.

In an embodiment, the reservoir and the first channel are each in connection with the flap cut in a hinge area of the flap.

In an embodiment, the reservoir extends to a depth of no less than 180 μm and no more than 220 μm or 250 μm from the anterior corneal surface.

In an embodiment, the reservoir is created temporarily prior to the first channel.

In an embodiment, the reservoir includes a channel-shaped portion that extends the first channel.

In an embodiment, the channel-shaped portion and the first channel have equal channel width at least in an area in which the channel-shaped portion is connected with the first channel.

In an embodiment, the reservoir includes a portion that extends the first channel along a straight line with respect to the first channel. In an alternate embodiment, the reservoir includes a portion that extends the first channel at an angle with respect to the first channel. In this embodiment, the portion may be tilted with respect to the first channel towards the anterior surface of the cornea or in a direction away from the anterior surface of the cornea.

In an embodiment, the first channel and the reservoir are mutually unconnected.

In an embodiment, the reservoir includes an annularly extending portion connected with the flap cut along an inner peripheral edge of the annularly extending portion. In this embodiment, the annularly extending portion may be shaped as a full annulus enclosing the flap cut entirely or as a part-annulus.

In an embodiment, the reservoir includes a plurality of sections, wherein mutually adjacent sections of the plurality are connected to each other at a bend.

In an embodiment, the flap cut includes a bed cut defining a stromal bed for the flap and a lateral cut extending from the bed cut towards the anterior corneal surface, wherein the first channel and the reservoir are connected with the bed cut at a peripheral portion thereof.

The present invention also provides a method of creating incisions in a human cornea, the method comprising: directing pulsed laser radiation at a human cornea; photodisrupting the cornea with the laser radiation to create in the cornea a flap cut defining a corneal flap that is connected to surrounding corneal tissue through a hinge, and one or more auxiliary cuts in connection with the flap cut for removing gas generated during creation of the flap cut, wherein the one or more auxiliary cuts define a first channel extending from the flap cut to an anterior surface of the cornea and a reservoir located at least partially deeper within the cornea than the flap cut.

In certain embodiments, a tangible computer-readable medium stores computer code for refractive correction that, when executed by a computer, is configured to control a focus of pulsed laser radiation having ultrashort pulses. The computer code is configured to bring about, when executed by the computer, a flap cut defining a corneal flap that is connected to surrounding corneal tissue through a hinge, and one or more auxiliary cuts in connection with the flap cut for removing gas generated during creation of the flap cut, wherein the one or more auxiliary cuts define a first channel extending from the flap cut to an anterior surface of the cornea and a reservoir located at least partially deeper within the cornea than the flap cut.

Embodiments of the present disclosure will now be described by way of example in greater detail with reference to the attached drawings, in which:

FIGS. 4-6 illustrate cross-sections of further examples of a corneal incision pattern;

FIG. 7 illustrates a top view of the exemplary corneal incision pattern of FIG. 6;

FIGS. 8 and 9 illustrate cross-sections of further examples of a corneal incision pattern;

Figure 1:
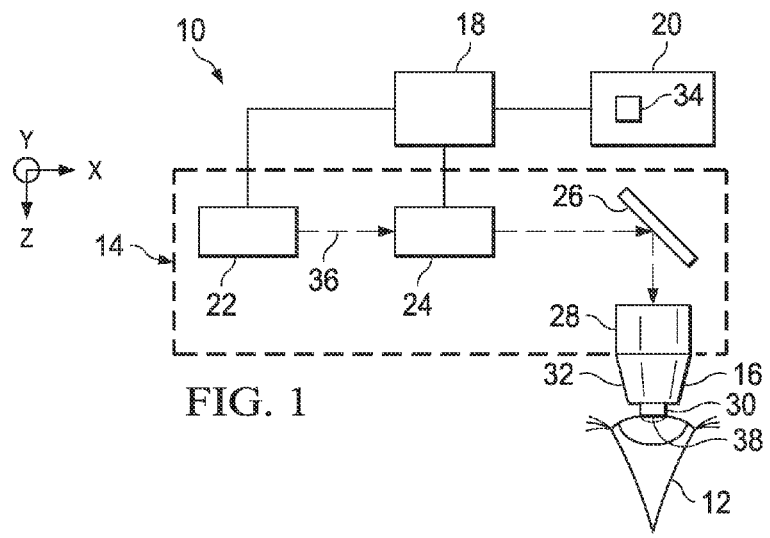
FIG. 1 illustrates an example of an apparatus for creating a flap incision in a human cornea according to an embodiment.

Referring now to the drawings, example embodiments of the disclosed apparatus and method are shown in detail. The following description is in no way intended to be exhaustive or to otherwise limit or restrict the accompanying claims to the specific embodiments shown in the drawings and disclosed herein. Although the drawings represent possible embodiments, the drawings are not necessarily to scale and certain features may be simplified, exaggerated, removed, or partially sectioned to better illustrate the embodiments. In addition, certain drawings may be in schematic form.

FIG. 1 illustrates an example embodiment of an apparatus 10 configured to create a corneal flap. In this embodiment, the apparatus 10 includes a laser device and a control computer. The laser device can create a flap in the cornea of a human eye using ultrashort-pulsed laser radiation. As used herein, ultrashort is intended to mean a pulse duration within the nanosecond, picosecond, femtosecond or attosecond range. The laser device can create the flap as part of a LASIK treatment, which reshapes the anterior surface of the cornea according to a refractive correction profile by means of ablation of stromal tissue.

The laser device may include controllable components that direct a focus of the pulsed laser radiation along a predetermined path within the cornea to create a vent channel and a reservoir to avoid the generation of an opaque bubble layer when the flap is created. The control computer instructs the controllable components to create the vent channel, the reservoir and a flap incision defining the corneal flap. In certain embodiments, the flap incision may include a bed cut defining a stromal bed for the flap and a lateral cut to form a lateral side of the flap. The vent channel allows gases generated during creation of the flap incision to be conducted away to the exterior of the eye. In certain embodiments, the vent channel is in connection with the bed cut of the flap incision. The reservoir extends at least partially deeper into the corneal tissue than the flap incision. Gases generated during creation of the flap incision can accumulate in the reservoir and may subsequently be absorbed by surrounding corneal tissue.

In the illustrated example of FIG. 1, the apparatus 10 performs laser surgery on a human eye 12. The apparatus 10 includes a laser device 14, a patient adapter 16, a control computer 18, and a memory 20, which may be coupled as shown. The laser device 14 includes a laser source 22, a scanner 24, one or more optical mirrors 26, and a focusing objective 28, which may be coupled as shown. The patient adapter 26 includes a contact element 30 and a support sleeve 32, which may be coupled as shown. The memory 20 stores a control program 34.

The laser source 22 generates a laser beam 36 with ultrashort pulses. The focal point of the laser beam 36 may create a laser-induced optical breakdown (LIOB) in tissues such as the cornea of the eye 12. The laser beam 36 may be precisely focused to allow for precise incisions in the corneal cell layers, which may reduce or avoid unnecessary destruction of other tissue.

The laser beam 36 may have any suitable wavelength, such as a wavelength in the range of 300-1900 nanometers (nm), for example, a wavelength in the range of 300-650, 650-1050, 1050-1250, or 1100-1900 nm. The laser beam 36 may also have a relatively small focus volume, e.g., 5 micrometers (μm) or less in diameter. In certain embodiments, the laser source 22 and/or a delivery channel (not shown in the drawings) for the laser beam 36 may be in a vacuum or near vacuum.

The scanner 24, optical mirrors 26, and focusing objective 28 are in the beam path of the laser beam 36. The scanner 24 is configured to transversely and longitudinally control the focal point of the laser beam 36. "Transverse" refers to a direction at right angles to the direction of propagation of the laser beam 36, and "longitudinal" refers to the direction of beam propagation. The transverse plane may be designated as the x-y plane, and the longitudinal direction may be designated as the z-direction.

The scanner 24 may transversely direct the laser beam 36 in any suitable manner. For example, the scanner 24 may include a pair of galvanometrically actuated scanner mirrors that can be tilted about mutually perpendicular axes. As another example, the scanner 24 may include an electro-optical crystal that can electro-optically steer the laser beam 36. The scanner 24 may longitudinally direct the laser beam 36 in any suitable manner. For example, the scanner 24 may include a longitudinally adjustable lens, a lens of variable refractive power, or a deformable mirror that can control the z-position of the beam focus. The focus control components of the scanner 24 may be arranged in any suitable manner along the beam path, e.g., in the same or different modular units.

The one or more optical mirrors 26 direct the laser beam 36 towards the focusing objective 28. For example, an optical mirror 26 may be an immovable deviating mirror. As an alternative, an optical element that can refract and/or diffract the laser beam 36 may be provided in place of, or in addition to, an optical mirror 26.

The focusing objective 28 focuses the laser beam 36 onto the eye 12 and more specifically onto a cornea of the eye 12. The focusing objective 28 may be separably coupled to the patient adapter 16. The focusing objective 28 may be any suitable optical device, such as an f-theta objective.

The patient adapter 16 interfaces with the cornea of the eye 12. The sleeve 32 couples to the focusing objective 28 and retains the contact element 30. The contact element 30 is transparent or translucent to the laser radiation and has an abutment face 38 that interfaces with the cornea and may level a portion of the cornea. In certain embodiments, the abutment face 38 is planar and forms a planar area on the cornea. The abutment face 38 may be on an x-y plane, so that the planar area is also on an x-y plane. In other embodiments, the abutment face need not be planar, e.g., may be convex or concave.

The control computer 18 controls controllable components, e.g., the laser source 22, scanner 24, and optionally one or more of the mirrors 26, in accordance with the control program 34. The control program 34 contains computer code that instructs the controllable components to focus the pulse laser radiation at a region of the cornea to photodisrupt at least a portion of the region.

In certain examples of operation, the scanner 24 may direct the laser beam 36 to form incisions of any suitable geometry. Examples of types of incisions include bed incisions and lateral incisions. A bed incision is a two-dimensional incision that is typically on an x-y plane (in a state when the cornea is flattened through abutment against the abutment face 38 of the contact element 30). The scanner 24 may form a bed incision by focusing the laser beam 36 at a constant z-value under the abutment face 38 and moving the focus in a pattern in an x-y plane. A lateral incision (or "side cut") is an incision that extends from under the anterior corneal surface (such as from a bed incision) to the surface. The scanner 24 may form a lateral incision by changing the z-value of the focus of the laser beam 36 and optionally changing the x and/or y values.

Any suitable portion of the cornea may be photodisrupted. One or more of any of the corneal layers may be selected for photodisruption. In addition, a portion of a cell layer may be photodisrupted in the z-direction, but part of the cell layer may remain on the cornea. Moreover, a particular area (or "target zone") in an x-y plane may be selected for photodisruption. For example, a target zone that forms a bed incision may be photodisrupted.

The apparatus 10 may photodisrupt a corneal layer in any suitable manner. In certain embodiments, the control computer 18 may instruct the laser device 14 to focus the laser beam 36 at a constant z-value under the abutment face 38 and move in a pattern in an x-y plane that substantially covers the target zone. Any suitable pattern may be used. For example, according to a meander pattern having rectilinear meander lines, the scan path has a constant y-value and moves in the +x direction. When the scan path reaches a point of the border of the target zone, the path moves to a next y-value that is a predetermined distance from the previous y-value and then moves in the −x direction until it reaches another point of the border. The scan path continues until the entire target zone is scanned. As another example, according to a spiral pattern, the scan path starts at or near the center of the target zone and moves in a spiral pattern until the path reaches the border of the target zone, or vice-versa. As yet another example, a plurality of concentric circles may be used to define a scan path for the laser beam 36.

As the laser beam 36 travels along the scan path, the laser radiation pulses create microdisruptions in the corneal tissue of the eye 12. In certain situations, a scan path pattern may yield a non-uniform distribution of microdisruptions over the target zone. In these cases, the laser beam 36 may be modified to make the distribution more uniform. For example, certain pulses may be blocked or the pulse energy may be decreased to reduce the number of or the effect of the pulses in a particular region.

Figure 2:
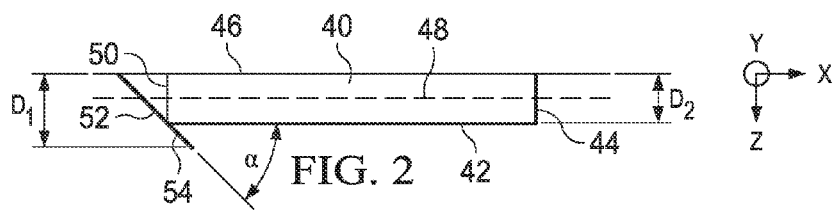
FIG. 2 illustrates a cross-section (taken along an x-z plane) of an exemplary corneal incision pattern.
Figure 3:
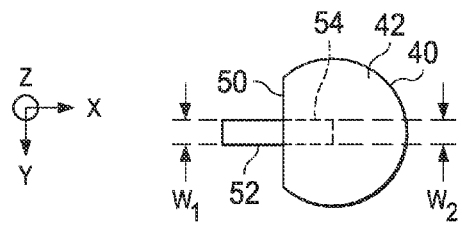
FIG. 3 illustrates a top view (viewed along a z-direction) of the corneal incision pattern of FIG. 2.

FIGS. 2 and 3 illustrate a first example of creating a corneal flap, which may be useful for performing a LASIK operation on the eye 12. The flap is denoted 40 and is formed by a bed incision 42 and a lateral incision 44 together. In the situation illustrated in FIG. 2, the cornea is flattened by abutment against the abutment face 38 of the patient adapter 16. An anterior surface of the cornea is denoted 46 and is shown leveled in FIG. 2. The leveling region in which the cornea is leveled as a consequence of its abutment against the abutment face 38 may be circular or may have a shape deviating from a circle.

The bed incision 42 and the lateral incision 44 together form a flap incision which delineates the flap 40 from surrounding corneal tissue. In the leveled state shown in FIG. 2, the bed incision 42 is a planar, two-dimensional incision and is on an x-y plane. The bed incision 42 is created at a depth of the cornea corresponding to the desired thickness of the flap 40. The thickness of the flap 40 may have any suitable value in the range from 60 μm to 150 μm, e.g., 60 μm, 80 μm, 100 μm, 120 μm or 150 μm. In certain embodiments, the bed incision 42 is created in the stromal tissue of the cornea. In the illustrated example of FIG. 2, the bed incision 42 is a stromal cut which is under the Bowman's layer of the cornea. A dashed line 48 in FIG. 2 indicates the Bowman's layer.

The bed incision 42 may have an outline of any suitable shape, depending on the desired shape of the flap 40. For example, the bed incision 42 may have a circular outline, as illustrated in FIG. 3. In FIG. 3, the bed incision 42 extends over an incomplete circular area in that it is shortened by a segment of a circle and terminates at a chord of a circle. It will be understood that in alternate embodiments, the bed incision 42 may extend over a complete circular area or may have a non-circular outline, e.g., an elliptical outline.

The lateral incision 44 extends along a partial periphery of the bed incision 42 and extends from the bed incision 42 to the anterior corneal surface 46. The lateral incision 44 is also created in the leveled state of the cornea, i.e. with the eye 12 bearing against the abutment face 38. In the example illustrated in FIG. 2, the lateral incision 44 extends at a right angle from the bed incision 42 toward the anterior surface 46 of the cornea. In other embodiments, the lateral incision 44 may extend obliquely, either inwards or outwards, from the bed incision 42 toward the anterior surface 46.

In the part of the periphery of the bed incision 42 not encompassed by the lateral incision 44, the flap 40 is still connected to the surrounding corneal tissue. The transition region between the flap 40 and the surrounding corneal tissue forms a hinge which permits the flap 40 to be folded away in order to expose the underlying tissue for an ablating laser treatment. The hinge line is, at least in sufficient approximation, rectilinear and is denoted 50 in FIGS. 2 and 3.

Photodisruptive treatment of human corneal tissue using pulsed laser radiation may cause the generation of gases as a result of the vaporization of the tissue. By appropriate selection of the radiation parameters of the laser radiation, the amount of gas that is generated can be reduced. It has been found, however, that in some cases the generation of gas cannot be avoided completely. While some of the generated gas may be absorbed by surrounding tissue, the inventors have observed that oftentimes not all of the gas is absorbed. Gases that remain unabsorbed may cause the generation of an opaque bubble layer (OBL), which may deteriorate the tracking precision of an eye-tracker during a subsequent ablating laser treatment of the eye. In certain circumstances, the OBL may even render impossible the tracking of the eye. In such instances, the surgeon may either force the OBL out of the corneal tissue manually by means of a suitable instrument or may have to wait for the OBL to disappear naturally.

To reduce the risk of OBL generation, the incision pattern according to the example embodiment of FIGS. 2 and 3 includes, in addition to the flap incision, an auxiliary incision pattern defining a vent channel 52 and a reservoir 54. The vent channel 52 allows gases generated during creation of the bed incision 42 to be discharged to the exterior of the eye 12. The vent channel 52 is connected with the bed incision 42 at the periphery thereof. In the illustrated example of FIGS. 2 and 3, the connection of the vent channel 52 with the bed incision 42 is in the region of the hinge line 50. In other embodiments, the vent channel 52 may be connected with the bed incision 42 in other portions of the periphery of the bed incision 42.

The vent channel 52 may have any suitable size and shape. In the example shown in FIG. 3, the vent channel 52 has a width $w_1$ that is the same from end to end. In other examples, the vent channel 52 may have a narrower width towards the bed incision 42 and a wider width towards the opposite end of the vent channel 52, or vice-versa. The vent channel 52 extends from the bed incision 42 to the anterior surface 46 of the cornea to thereby establish a gas discharge path allowing gases to be led away from the bed incision 42 toward the outside of the eye. The width of the vent channel 52 at any position along its extension from the bed incision 42 to the anterior corneal surface 46 may have any suitable value, such as a value in the range from 1-5 mm or 1.5-4 mm or 2-3.5 mm. In the leveled state shown in FIG. 2, the vent channel extends rectilinearly from the bed incision 42 to the anterior corneal surface 46 when viewed in a cross-section orthogonal to an x-y plane. In other examples, the vent channel may extend in a different manner from the bed incision 42 to the anterior corneal surface 46, e.g., in a curved manner.

While the vent channel 52 establishes a vent path to the exterior of the eye 12, the reservoir 54 is entirely under the anterior corneal surface 46. At least a portion of the reservoir 54 is located deeper within the cornea than the bed incision 42. In certain embodiments, the entire reservoir 54 is located deeper within the cornea than the bed incision 42.

The reservoir 54 is connected with the bed incision 42 at the periphery thereof. In the illustrated example of FIGS. 2 and 3, the connection of the reservoir 54 with the bed incision 42 is in the same region of the periphery of the bed incision 42 where the vent channel 52 is connected with the bed incision 42. In other words, the vent channel 52 and the reservoir 54 have overlapping areas of connection with the bed incision 42, so that gases collected in the reservoir 54 may be removed from the reservoir 54 either through absorption in surrounding corneal tissue or via the vent channel 42 to the outside. In other examples, connections of the vent channel 52 and the reservoir 54 with the bed incision 42 may be established in different, non-overlapping portions of the periphery of the bed incision 42, so that no direct connection of the reservoir 54 with the vent channel 52 exists.

It has been found by the inventors that the combination of the vent channel 52 and the reservoir 54 is effective to substantially reduce the risk of OBL generation in the flap 40 and/or in the stromal bed under the flap 40. While the vent channel 52 can be viewed as a chimney to lead a major portion of the generated gases away from the bed incision 42 toward the exterior, the reservoir 54 may serve to release the vent channel 52 from overload and provide an additional means for removing gases from the bed incision 42. Moreover, if the venting function of the vent channel 52 is restricted or suppressed (such as, e.g., by an occlusion of the vent channel 52 for anatomical reasons) the reservoir 54 provides a back-up space to collect gases generated during creation of the bed incision 42.

In certain embodiments, the reservoir 54 extends to a depth of at least 150 μm and no more than 300 μm or 250 μm from the anterior corneal surface 46. For example, the reservoir 54 extends to a maximum depth of 150-170 μm, 170-190 μm, 190-210 μm, 210-230 μm, 230-250 μm or 250-300 μm from the anterior corneal surface 46. A depth $d_1$ in FIG. 2 denotes the maximum depth of the reservoir 54. Further, a depth $d_2$ in FIG. 2 denotes the depth of the bed incision 42 (corresponding to the thickness of the flap 40). The thickness $d_2$ may have any suitable value. Example values for $d_2$ are between 90 and 200 μm.

Preferably, the reservoir 54 extends no deeper than 250 μm (measured from the anterior corneal surface 46) to avoid that gases, via the reservoir 54 and such structures as blood vessels and/or Schlemm's channel, spread into the anterior chamber of the eye 12.

In the embodiment shown in FIG. 2, the reservoir 54 extends from the periphery of the bed incision 42 at an angle α (alpha) inwardly under the bed incision 42. The angle α (measured with respect to an x-y plane) may have any suitable value. For example, the value of the angle α may be selected so that tan α (tangent of alpha) has a value anywhere in a range from 0.15-0.3, 0.17-0.27, or 0.2-0.24.

In the example embodiment of FIGS. 2 and 3, the reservoir 54 is shaped as a channel having a width $w_2$. The width $w_2$ may have any suitable value, such as a value in any of the ranges indicated further above for the value of the width $w_1$. In the example of FIG. 3, the channel-shaped reservoir 54 has the same width $w_2$ from end to end.

In the example shown in FIG. 2, the reservoir 54 extends the vent channel 52 along a straight line. In other words, the vent channel 52 extends at the same angle α with respect to an x-y plane as the reservoir 54. The vent channel 52 and the reservoir 54 enclose an angle of 180 degrees in the illustrated embodiment of FIG. 2, in the leveled state of the cornea.

Figure 4:
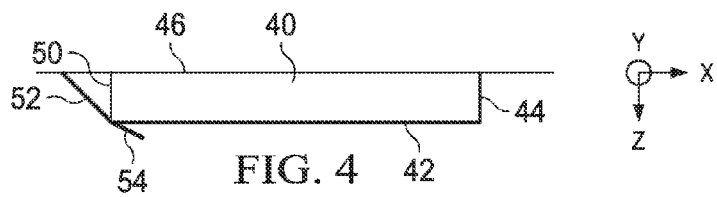
Figure 5:
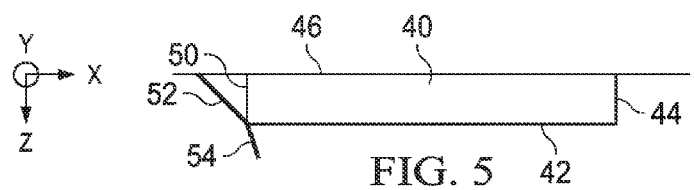

Other embodiments featuring a channel-shaped reservoir 54 are shown in FIGS. 4 and 5 wherein the vent channel 52 and the reservoir 54 enclose an angle that is different from 180 degrees. In FIG. 4, the reservoir 54 is inclined with respect to the vent channel 52 toward an x-y plane. In FIG. 5, the reservoir 54 is inclined with respect to the vent channel 52 in a direction away from an x-y plane. In other embodiments, the reservoir 54 may be oriented at right angles with respect to an x-y plane, in the leveled state of the cornea. In such embodiments, the value of the angle α will be 90 degrees.

In certain embodiments, the reservoir 54 includes a plurality of sections of different shapes and/or different orientations. In such embodiments, the reservoir 54 may have a bend at the interconnection of two adjacent sections. The reservoir 54 may have any number of sections, e.g., two or three or four.

In the example embodiment illustrated in FIGS. 6 and 7, the reservoir 54 includes a first section 56 and a second section 58. The first section 56 extends from the periphery of the bed incision 42 and is shaped as a straight, planar channel. The second section 58 extends from the first section 56 and is shaped as a pocket extending over a part of a circular area. In the illustrated example of FIG. 7, the second section 58 extends over approximately a semi-circular area, wherein the circle diameter is larger than the width $w_2$ of the channel-shaped first section 56. In other embodiments, the second section 58 may have a channel shape and may have a channel width that is the same as the width $w_2$ of the first section 56 or is different from the width $w_2$. In general, any suitable shape may be chosen for the second section 58.

The second section 58 is illustrated in FIG. 6 as being oriented parallel to an x-y plane and is connected to the end of the first section 56 that is remote from the periphery of the bed incision 42. The second section 58 extends in an outward direction from its connection with the first section 56, i.e. away from the flap 40.

In FIG. 8, the reservoir 54 includes a first section 60, a second section 62 and a third section 64. The first section 60 extends from the periphery of the bed incision 42 to deeper within the cornea at right angles with respect to an x-y plane. The second section 62 extends the first section and is on an x-y plane. The third section 64 extends from the second section 62 at a right angle with respect to the second section 62 and extends upward toward the anterior surface 46 of the cornea. Any suitable shape may be chosen for each of the sections 60, 62, 64.

In FIG. 9, the reservoir 54 extends from the periphery of the bed incision 42 in an oblique outward direction.

Figure 10:
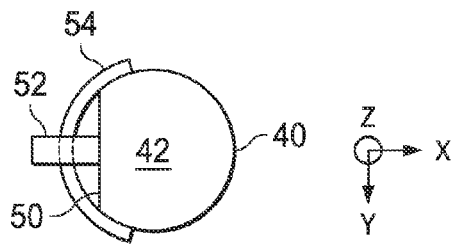
FIGS. 10-13 illustrate top views of further examples of a corneal incision pattern.
Figure 11:
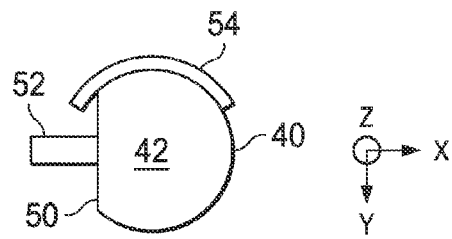
Figure 12:
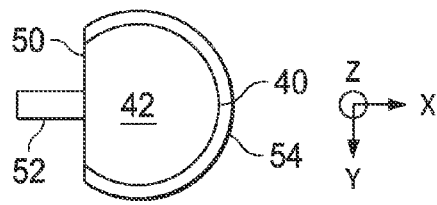

FIGS. 10, 11 and 12 illustrate embodiments in which the vent channel 52 and the reservoir 54 are connected with the bed incision 42 in different regions thereof without direct interconnection. The reservoir 54 is shaped as a part-annular pocket connected at its inner circumference with the bed incision 42. In FIG. 10, the reservoir 54 overlaps with the vent channel 52 when viewed in the z-direction, whereas in FIG. 11 no overlap exists between the reservoir 54 and the vent channel 52 in the z-direction. In FIG. 12, the reservoir 54 extends over the entire periphery of the bed incision 42, except for the region of the hinge (as represented by the hinge line 50).

Figure 13:
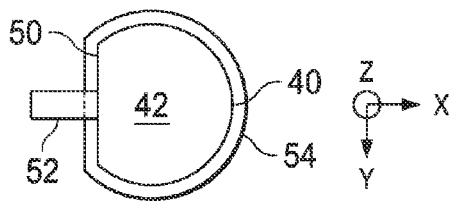

FIG. 13 illustrates an example embodiment in which the reservoir 54 extends over the entire periphery of the bed incision 42 (including the hinge line 50).

In all embodiments described herein, the reservoir 54 may be created before the vent channel 52 is created. In certain embodiments, the reservoir 54 is created starting at its end farthest from the bed incision 42 and continuing towards its end situated adjacent the bed incision 42. In other embodiments, the reservoir 54 is created starting at its end closest to the bed incision 42 and continuing to its end farthest from the bed incision 42. The vent channel 52 may be created starting at the anterior corneal surface 46 and continuing towards the bed incision 42, or vice-versa. According to alternate embodiments, the reservoir 54 can be created temporarily after the vent channel 52.

Figure 14:
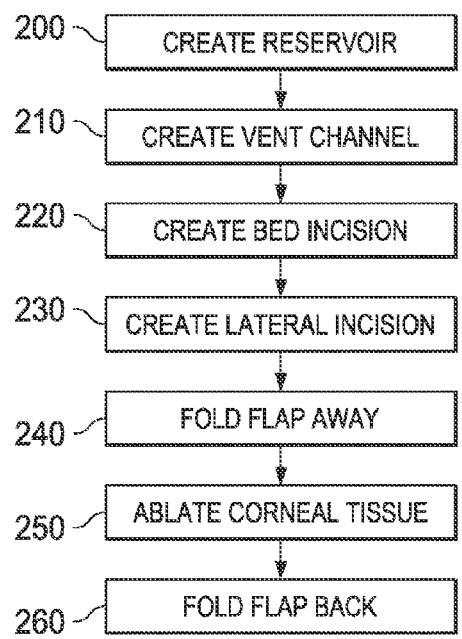
FIG. 14 illustrates an example of a method for LASIK of a human eye according to an embodiment.

FIG. 14 shows an example of a method for performing a refractive laser treatment of the eye 12, such as in a LASIK operation. The method may be performed by the apparatus 10 of FIG. 1.

The method starts at step 200, where a reservoir 54 is created. The reservoir 54 can accept gases generated during subsequent phases of the laser treatment. A vent channel 52 is created at step 210. The vent channel 52 allows gases to be removed to the exterior of the eye 12. The temporal order of the steps 200 and 210 may be reversed in certain embodiments. A bed incision 42 is created at step 220. Gases generated during the creation of the bed incision 42 can disperse into the reservoir 54 and the vent channel 52 to thereby avoid the generation of an OBL in the corneal material underlying or overlying the bed incision 42. A lateral incision 44 is created at step 230. The lateral incision 44 and the bed incision 42 together define a corneal flap 40.

The flap 40 is then folded away at step 240 to thereby expose an area of corneal tissue. The exposed area is ablated at step 250 according to a pre-defined ablation profile using UV laser radiation. After termination of the ablating laser treatment, the flap 40 is folded back over the ablated tissue area at step 260.

The invention claimed is:

1. An apparatus for creating incisions in a human cornea, the apparatus comprising:
    a source of pulsed laser radiation;
    a scanner device for scanning the laser radiation;
    a control computer for controlling the scanner device based on a control program, the control program containing instructions that, when executed by the computer, bring about the creation in the cornea of:
        a flap cut defining a corneal flap that is connected to surrounding corneal tissue through a hinge, the flap cut comprising a bed cut and a lateral cut, the bed cut defining a stromal bed for the flap, the lateral cut extending from the bed cut towards an anterior surface of the cornea; and
        one or more auxiliary cuts in connection with the flap cut for removing gas generated during creation of the flap cut, the one or more auxiliary cuts defining:
            a vent channel extending from the flap cut to the anterior surface of the cornea; and
            a reservoir located at least partially deeper within the cornea than the bed cut, the reservoir having a first end and a second end opposite of the first end, the first end connected to the bed cut, the second end separated from the bed cut, the vent channel and the reservoir having overlapping areas of connection with the bed cut to allow the vent channel to remove gases collected in the reservoir to the outside.

2. The apparatus of claim 1, wherein the reservoir and the vent channel are each connected with the flap cut in a hinge area of the flap.

3. The apparatus of claim 1, wherein the reservoir extends to a depth of at least 180 µm and no more than 250 µm from the anterior corneal surface.

4. The apparatus of claim 1, wherein the instructions, when executed by the computer, bring about the creation of the reservoir temporally prior to the vent channel.

5. The apparatus of claim 1, wherein the reservoir includes a channel-shaped portion that extends the vent channel.

6. The apparatus of claim 5, wherein the channel-shaped portion and the vent channel have equal channel width at least in an area in which the channel-shaped portion is connected with the vent channel.

7. The apparatus of claim 1, wherein the reservoir includes a portion that extends the vent channel along a straight line with respect to the vent channel.

8. The apparatus of claim 1, wherein the reservoir includes a portion that extends the vent channel at an angle with respect to the vent channel.

9. The apparatus of claim 7, wherein the portion is tilted with respect to the vent channel towards the anterior surface of the cornea.

10. The apparatus of claim 7, wherein the portion is tilted with respect to the vent channel in a direction away from the anterior surface of the cornea.

11. The apparatus of claim 1, wherein the reservoir includes an annularly extending portion connected with the flap cut along an inner peripheral edge of the annularly extending portion.

12. The apparatus of claim 11, wherein the annularly extending portion is shaped as a full annulus enclosing the flap cut entirely.

13. The apparatus of claim 11, wherein the annularly extending portion is shaped as a part-annulus.

14. The apparatus of claim 1, wherein the reservoir includes a plurality of sections, wherein mutually adjacent sections of the plurality are connected to each other at a bend.

15. The apparatus of claim 1, wherein the vent channel and the reservoir are connected with the bed cut at a peripheral portion thereof.

16. A method of creating incisions in a human cornea, the method comprising:
directing pulsed laser radiation at a human cornea;
photodisrupting the cornea with the laser radiation to create in the cornea:
a flap cut defining a corneal flap that is connected to surrounding corneal tissue through a hinge, the flap cut comprising a bed cut and a lateral cut, the bed cut defining a stromal bed for the flap, the lateral cut extending from the bed cut towards an anterior surface of the cornea; and
one or more auxiliary cuts in connection with the flap cut for removing gas generated during creation of the flap cut, wherein the one or more auxiliary cuts define:
a vent channel extending from the flap cut to the anterior surface of the cornea; and
a reservoir located at least partially deeper within the cornea than the bed cut, the reservoir having a first end and a second end opposite of the first end, the first end connected to the bed cut, the second end separated from the bed cut, the vent channel and the reservoir having overlapping areas of connection with the bed cut to allow the vent channel to remove gases collected in the reservoir to the outside.

17. The method of claim 16, wherein the reservoir and the vent channel are each in connection with the flap cut in a hinge area of the flap.

18. The method of claim 16, wherein the reservoir extends to a depth of at least 180 µm and no more than 250 µm from the anterior corneal surface.

19. The method of claim 16, wherein the reservoir is created temporally prior to the vent channel.

20. The method of claim 16, wherein the reservoir includes a channel-shaped portion that extends the vent channel.

21. The method of claim 16, wherein the channel-shaped portion and the vent channel have equal channel width at least in an area in which the channel-shaped portion is connected with the vent channel.

22. The method of claim 16, wherein the reservoir includes a portion that extends the vent channel along a straight line with respect to the vent channel.

23. The method of claim 16, wherein the reservoir includes a portion that extends the vent channel at an angle with respect to the vent channel.

24. The method of claim 23, wherein the portion is tilted with respect to the vent channel towards the anterior surface of the cornea.

25. The method of claim 23, wherein the portion is tilted with respect to the vent channel in a direction away from the anterior surface of the cornea.

26. The method of claim 16, wherein the reservoir includes an annularly extending portion connected with the flap cut along an inner peripheral edge of the annularly extending portion.

27. The method of claim 26, wherein the annularly extending portion is shaped as a full annulus enclosing the flap cut entirely.

28. The method of claim 26, wherein the annularly extending portion is shaped as a part-annulus.

29. The method of claim 16, wherein the reservoir includes a plurality of sections, wherein mutually adjacent sections of the plurality are connected to each other at a bend.

30. The method of claim 16, wherein the vent channel and the reservoir are connected with the bed cut at a peripheral portion thereof.

* * * * *